(12) United States Patent
Sanchez Ramos

(10) Patent No.: US 7,703,917 B2
(45) Date of Patent: *Apr. 27, 2010

(54) THERAPEUTIC PROPHYLACTIC OPHTHALMOLOGIC LENS FOR PSEUDOAPHAKIC EYES AND/OR EYES SUFFERING NEURODEGENERATION

(75) Inventor: Celia Sanchez Ramos, Madrid (ES)

(73) Assignee: Universidad Complutense De Madrid, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 11/651,402

(22) Filed: Jan. 9, 2007

(65) Prior Publication Data

US 2007/0188701 A1 Aug. 16, 2007

Related U.S. Application Data

(60) Provisional application No. 60/790,759, filed on Apr. 10, 2006.

(30) Foreign Application Priority Data

Jan. 10, 2006 (ES) ................................ 200600052

(51) Int. Cl.
*G02C 7/06* (2006.01)
(52) U.S. Cl. ...................................... 351/177; 351/163
(58) Field of Classification Search ................... 351/44, 351/45, 162, 163, 164, 165
See application file for complete search history.

(56) References Cited

U.S. PATENT DOCUMENTS 5,528,322 A * 6/1996 Jinkerson ..................... 351/163

* cited by examiner

*Primary Examiner*—Scott J Sugarman
(74) *Attorney, Agent, or Firm*—Ladas and Parry LLP

(57) ABSTRACT

The object of this invention is an ophthalmologic lens for pseudoaphakic eyes and/or eyes suffering macular and retinal degeneration, created by applying a yellow pigment filter to a regular ophthalmologic lens, to protect the eye from the short wavelengths of the visible spectrum (under 500 nm). This invention avoids the difficulties and risks of the techniques currently available to protect eyes subjected to cataract surgery and improves protection in eyes with neurodegeneration through the simple use of an ophthalmologic lens.

The invention is comprised of a common ophthalmologic lens and a yellow pigment that absorbs short wavelengths of light of 350/500 nm, both appropriate for use in humans.

2 Claims, No Drawings

THERAPEUTIC PROPHYLACTIC OPHTHALMOLOGIC LENS FOR PSEUDOAPHAKIC EYES AND/OR EYES SUFFERING NEURODEGENERATION

This application claims the benefit of U.S. Provisional Application No. 60/790,759 filed Apr. 10, 2006 and incorporates the same by reference.

OBJECT OF THE INVENTION

The invention is intended for the ophthalmology sector of the market. The object of this invention is an ophthalmologic lens for pseudoaphakic eyes (those that have undergone cataract surgery) and/or eyes with macular and retinal degeneration, produced by applying a yellow pigment to a conventional ophthalmologic lens, to protect the eye from the short wavelengths of the visible spectrum (<500 nm).

STATE OF THE TECHNIQUE

Visual perception is the result of the response to visible radiation in the wavelength range 380-760 nm. In the environment, solar radiation is the main risk factor for vision. The sun emits UV rays and IR radiation, mainly absorbed by the atmosphere. When the solar radiation transmitted through the atmosphere reaches the Earth's surface it consists of UV-B rays (230-300 nm), UV and UV-A rays (300-380 nm), visible light rays (380-760 nm) and IR rays (760-1400 nm). Healthy human eyes freely transmit IR rays and those of most of the visible spectrum to the retina, but the cornea and crystalline lens prevent the most reactive wavelengths of the visible spectrum (UV-B rays and the blue portion of the spectrum) from reaching the retina.

The human crystalline lens changes its transmission properties as it ages by intensifying its yellowish color thus increasing its capacity to filter out UV and blue light rays. Hence, in persons older than 65 years ultraviolet light (<400 nm) is not transmitted and the transmission of blue light (400-500 nm) is markedly reduced.

The retina is capable of protecting itself from short wavelengths of light in two ways: through its uneven distribution of photoreceptors, such that there are no photoreceptors sensitive to blue light in the macular depression; and through the actions of yellow pigments in this zone, which also exert a protective effect.

These natural protection systems the human eye has against the shortest wavelengths of light—the crystalline lens and structures of the retina—can be seriously affected by certain diseases and/or surgical procedures:

Cataracts, whose only surgical treatment involves the removal of the crystalline lens Additionally, it is common to find a pathological ageing process that causes degradation of the retinal structures producing age-related macular degeneration (AMD).

We should also consider that both cataracts and AMD can coexist in persons older than 65 years. In this population of elderly subjects, cataract is the main cause of vision loss and AMD is the main cause of blindness. In addition we should expect an increase in both these diseases due, among other factors, to our increased life expectancy. This translates into a great interest in these diseases and their treatment options in the research field and optical industry Several epidemiological studies have evaluated the relationship between cataract surgery and AMD. Klein (Klein R, Klein B E, Wong T Y, Tomany S C, Cruickshanks K J. The association of cataract and cataract surgery with the long-term incident of age-related maculopathy. Arch Ophthalmol 120:1551-1558.2002) and Freeman (Freeman E, Munoz B, West S K, Tielsch J M, Schein O D. Is there an association between cataract surgery and age-related macular degeneration. Am J Ophthalmolm 135(6): 849-856.2003) assure there is a higher risk of developing the symptoms of AMD in persons who have undergone cataract surgery. However, in earlier investigations by Wang (Wang J J, Mitchell P, Cumming R G, Lim R. Cataract and age-related maculopathy: the Blue Mountains Eye Study. Ophthalmic Epidemiol 6: 317-326.1999) and McCarty (McCarty C A, Mukesh B N, Fu C L, Mitchell P, Wang J J, Taylor H R. Risks factors for age-related maculopathy: the Visual Impairment Project. Arch Ophthalmol 119:1455-1462.2001) this hypothesis was rejected, possibly because of the less developed technology used for their diagnostic measurements.

Techniques such as optical coherence tomography that allow the accurate, rapid and non-invasive follow up of retinal neurodegeneration processes have only recently been introduced. These techniques are essential for establishing the determining effect of the natural pigments that absorb harmful radiations.

Several techniques have also been developed to protect eyes subjected to cataract surgery from short wavelengths of light:

There are several types of filter containing a yellow pigment on the market yet there is no optimal procedure and/or device to apply these filters to the human eye as a preventive and/or therapeutic measure to replace and/or improve the eye's natural protection Since the middle of the 1990's, eyes operated on for cataract extraction have been implanted with intraocular lenses containing a yellow pigment to act as a filter. This option requires surgical intervention with all its risks and difficulties. There is also a large population of subjects implanted with a transparent lens to replace the natural lens during cataract surgery who are therefore devoid of the necessary protection. In these patients, the artificial crystalline lens, lacking a yellow pigment, needs to be complemented with a system to support the yellow pigment, such as the ophthalmologic lens proposed here.

Several patents related with the state of this technique have been developed although these differ considerably from the object of the present invention:

An optical lens with selective transmission functions (Pat. No. RE38402) that, in the form of spectacles or contact lenses, orange in color, improves vision and reduces ocular damage in intensely illuminated places, substantially eliminating UV rays and blue light from 400 and 500 nm.

Polarizing lenses that block blue light and UV rays (U.S. Pat. No. 5,400,175), composed of a polarizer that horizontally blocks polarized light and a filter that blocks blue light and UV radiation.

Special optical filters for certain activities and optical accessories that use these filters (U.S. Pat. No. 6,893,127) that improve the visualization of objects, for example in sports activities.

Corrective contact lens also with a therapeutic effect (patent FR2761785), designed to correct myopia and strabismus through the use of dyes in certain areas to stimulate or de-stimulate particular zones of the retina.

Polarized contact lenses (U.S. Pat. No. 6,874,888) with a clear peripheral zone and a polarizing element that covers the pupil area and thus protects the eyes from the harmful rays of the sun and from other sources of potentially harmful light.

Safety contact lens (patent US2005024583), which through coatings or treatments, absorbs or reflects certain wavelengths, including one or more identification areas to ensure that the lens selected is appropriate for the use required.

Color contact lens for cataracts (patent JP11253480) designed to solve the problem of sunglasses, comprised of a pupil as in color contact lenses that simulates the effects of sunglasses, and an iris with patterns matching the color of the iris.

Contact lens designed to treat cyanopsia or blue vision disease (patent JP1204668) by introducing a yellow or orange compound capable of absorbing wavelengths of 320-450 nm to diminish the effects of this disease. Cyanopsia is a perception defect that gives rise to distorted color vision. To the patients, all objects appear blue. The lens attempts to improve this effect of perception but in no case tries to protect the retinal neurons from short wavelength radiation of less than 550 nm.

These patents differ from the present invention mainly in their purpose and utility since none has been designed to protect eyes subjected to cataract surgery or suffering neurodegeneration from short wavelengths of light.

DESCRIPTION OF THE INVENTION

The objective of the invention in the case of pseudoaphakic subjects is to functionally compensate for the removal of protective pigments (along with the natural lens during surgery) and in the case of neurodegeneration processes is to potentiate the prophylactic effect of the absorption of blue and ultra violet light using an ophthalmologic lens as support. As mentioned, it is very common that both these pathologies coexist in this population of elderly persons.

The invention consists of a therapeutic ophthalmologic lens for the treatment of eyes suffering neurodegeneration processes and/or pseudoaphakic eyes, produced by applying a yellow pigment to an ophthalmologic lens that acts as a filter absorbing short wavelengths of light of 350/500 nm.

The therapeutic ophthalmologic lens for pseudoaphakic eyes is therefore comprised of three elements:

A regular ophthalmologic lens for use in human eyes
A frame in which to mount the ophthalmologic lens
A yellow pigment, among those available on the market, compatible with the lens that absorbs short wavelengths of 350 to 500 nm, applied to the entire lens, resulting in a yellow ophthalmologic lens.

The lens can be of the specific dimensions adequate for each individual and can be mounted in any type of spectacle frame.

How to Prepare the Invention

There are several ways to prepare a tinted ophthalmologic lens as described in patents such as US20030164481 and U.S. Pat. No. 6,793,339. Its preparation is illustrated by the example described below although not limited to this method, there being many alternatives and combinations to manufacture this lens.

Example of how to prepare the invention:

10.3 mg of a conventional yellow dye, 4-phenylazophenol solvent yellow 7 (SY7) are dissolved in 10.01 g of a monomer solution containing 66% PEA, 30.5% PEMA and 3.3% BDDA, to give an SY7 concentration of 0.103 wt %

Next, 52.3 mg of bis 4-tert-butylcyclohexylperoxide dicarbonate are added as the polymerization catalyst.

Using a syringe, the solution is introduced in a mould made of two glass plates, joined together one over the other by metal clips, and a 1 mm Teflon ring. The solution is spread as 1 mm-thick sheets.

Polymerization occurs when the mould is placed in an oven at 65° C. for 17 hours. The oven temperature is then increased to 100° C. for a further 3 hours.

Once polymerized, the sheet is removed from the mould, checked for its absorption properties and then given its final shape.

In summary, by combining an ophthalmologic lens with a yellow dye, both presently available for use in human eyes, patients who have undergone cataract extraction with the implant of a clear intraocular lens will be able to compensate for the lack of protection of the operated eye by simply using an ophthalmologic lens, and those with retinal neurodegeneration will be able to improve their natural protection. The use of such a lens will avoid the problems related to the use of the options available on the market (filters not incorporated in a lens and intraocular lenses).

The invention claimed is:

1. A method for treating a patient with retinal neurodegeneration comprising:

(a) providing a therapeutic and prophylactic opthalmologic lens produced with a yellow pigment that absorbs short wavelength radiation in a range of 350-500 nm, said opthalmologic lens comprising a frame for mounting on the patient; and (b) mounting the frame on the patient so that the opthalmologic lens improves protection of an eye of the patient.

2. The method according to claim 1, wherein the patient is a human.

* * * * *